Figure 1:
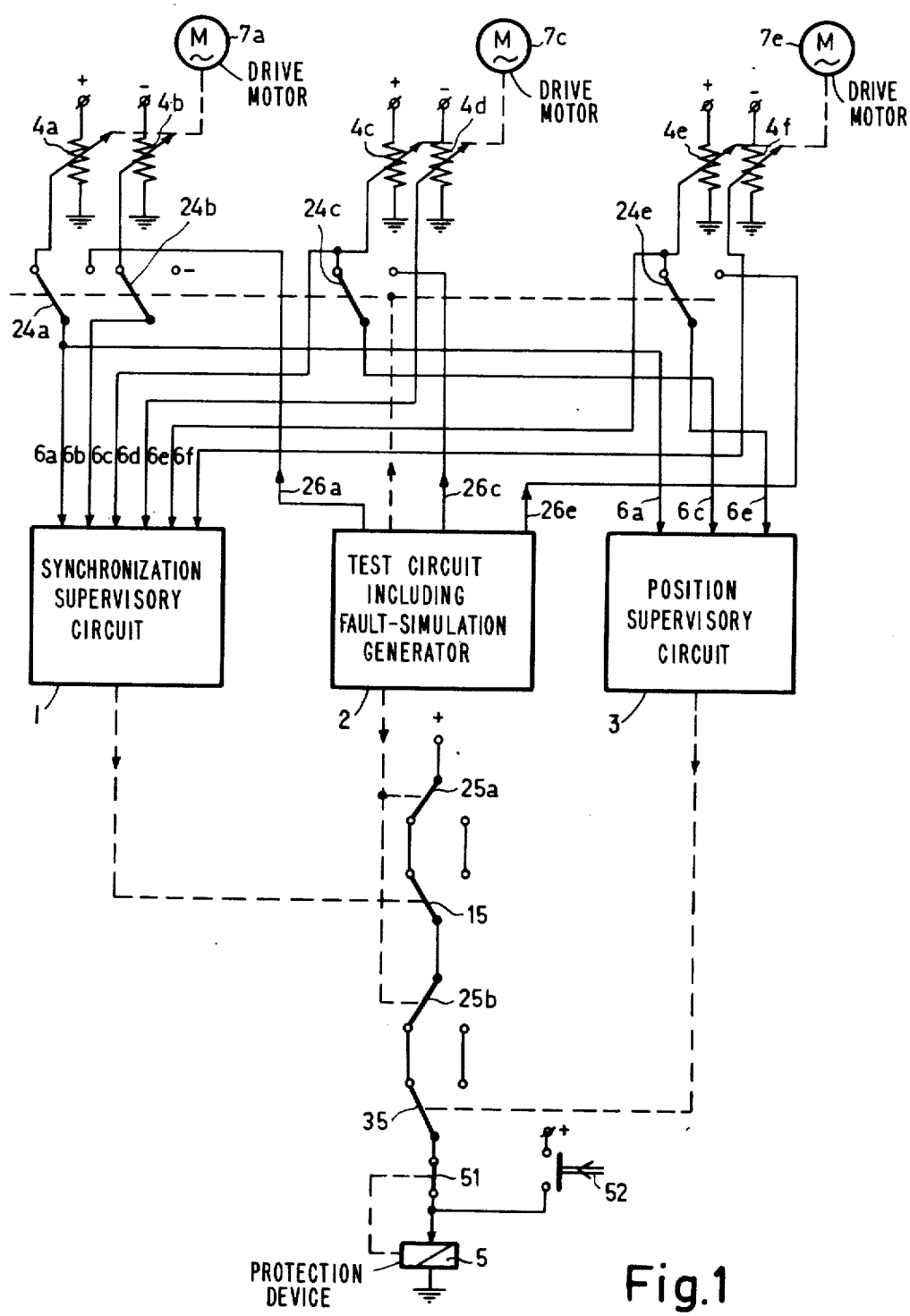

United States Patent [19]
Hecker

[11] 3,958,123
[45] May 18, 1976

[54] APPARATUS FOR AUTOMATICALLY TESTING X-RAY SUPERVISORY APPARATUS

[75] Inventor: Wolfgang Hecker, Hamburg, Germany

[73] Assignee: U.S. Philips Corporation, New York, N.Y.

[22] Filed: Apr. 2, 1974

[21] Appl. No.: 457,239

[30] Foreign Application Priority Data
Apr. 9, 1973 Germany............................ 2317744

[52] U.S. Cl. .............................................. 250/413
[51] Int. Cl.² .......................................... H05G 1/30
[58] Field of Search..................... 250/413, 414, 415

[56] References Cited
UNITED STATES PATENTS
3,038,998   6/1962   Bryer et al...................... 250/413 X

*Primary Examiner*—Davis L. Willis
*Attorney, Agent, or Firm*—Frank R. Trifari; Ronald L. Drumheller

[57] ABSTRACT

X-ray examining apparatus generally conprise various supervisory circuits which must prevent, for example, that the table top is lowered too far when the table is in the vertical position or that the pressure exerted on the patient becomes too high. The quantities to be supervised are simulated by the voltage to be derived from the potentiometer, and if such a potentiometer becomes defective it may occur that the supervisory device is not actuated. It is also possible that the supervisory circuit itself is defective. In order to detect such a defect, a fault-simulation generator is provided which during operation is connected at regular instants to the input of the supervisory circuit instead of to the potentiometer tapping and which generates voltages which correspond to a failure. If the supervisory circuit is not actuated in such a case, it means that it is defective. This defect can be signalled by the test circuit.

1 Claim, 4 Drawing Figures

APPARATUS FOR AUTOMATICALLY TESTING X-RAY SUPERVISORY APPARATUS

The invention relates to an X-ray examining apparatus comprising a test circuit for a suppervisory circuit which receives at least one voltage which is dependent of a quantity to be supervised and which is generated by at least one transducer, the said supervisory circuit actuating a switching circuit if the value of the voltage lies within a predetermined range (inhibited range). A supervisory circuit is to be understood to mean hereinafter an operation-supervisory circuit as well as a safety-supervisory circuit.

An operation-supervisory circuit serves to supervise a quantity during the operation of the apparatus and to actuate a switching circuit as soon as a critical situation occurs. For example, in X-ray examining apparatus in which the recording equipment can be moved towards the patient by way of a motor drive, an operation-supervisory circuit must be provided which switches off the motor drive as soon as the pressure exerted on the patient reaches a predetermined critical value. If a pressure transducer which is used for this purpose becomes defective, it may occur, of course, that the pressure exerted on the patient exceeds the critical value without the switching device for switching off the motor drive being actuated.

Therefore, usually an additional safety-supervisory circuit is provided which is actuated as soon as the quantity to be supervised slightly exceeds the critical limit value. The safety-supervisory circuit, consequently, is actuated only in the case of a failure of the operation-supervisory circuit. The switching circuit controlled by the safety-supervisory circuit is designed such that the operator of the X-ray apparatus cannot switch on the apparatus before the defect in the operation-supervisory circuit has been removed. For example, in X-ray examining apparatus in which the tilting position in which the patient's head is down is limited to for example 30°, the operation-supervisory circuit comprises a contact which is activated as soon as the apparatus reaches this 30°-position, the motor drive then being switched off. If this contact is not actuated in the case of a defect so that the motor is not switched off, a safety contact incorporated in the safety-supervisory circuit is actuated, with the result that the use of the apparatus is blocked in the described manner until the defect in the operation-supervisory circuit has been removed. Because the safety-supervisory circuit becomes active only in the case of a defect in the operation-supervisory circuit, it may occur that a defect in the safety-supervisory circuit is not discovered in the course of normal operation. If the safety-supervisory circuit also becomes defective, there is no protection whatsoever against any exceeding of the adjusted limit in the vertical position in which the patient's head is down, with the result that the apparatus or the patient can be damaged.

The use of modern detectors of small volume for picking-up the quantity to be supervised can increase the safety risk even further. For example, if the limit-position contacts are replaced by potentiometers whose tappings are adjusted by the motor for the displacement of components of the apparatus, in which case the voltage on the potentiometer tapping is a measure of the position of the component and the switching circuit is actuated when the voltage on the potentiometer tapping comes within a predetermined range (switching range), errors can occur in that the potentiometer tappings changes in the course of time or no longer makes contact, or because the electronics in the operation-supervisory circuit for measuring the voltage on the potentiometer fail.

The invention therefore has for its object to enhance the safety of a supervisory circuit for an X-ray examining apparatus.

To this end, an X-ray examining apparatus of the kind set forth is characterized in that the test circuit comprises a generator for generating voltages which are associated with the inhibited range and controls switches which connect the input of the supervisory circuit alternately to the transducer and to the generator and which at the same time control the switching circuit such that when it is connected to the generator it is actuated only in the case of a defect in the supervisory circuit. Thus, according to the invention the input of the (operation and/or safety) supervisory circuit is constantly switched over between the connected transducer and a generator which generates voltages in a predetermined range so that defects are simulated. When the input of the supervisory circuit is connected to the generator, the supervisory circuit should generate a signal — if it is ready for operation — which would actuate the switching circuit when the supervisory circuit is connected to the converter; however, this is not desirable in the operational-supervisory circuit. Therefore, at the same time the switching circuit is controlled such that — when it is connected to the generator — it is actuated only in the case of a defective supervisory circuit.

Figure 2:
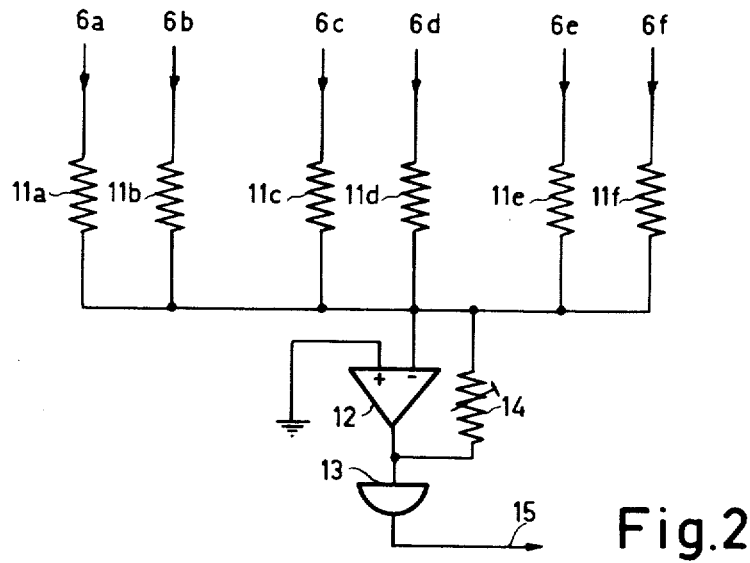
Figure 3:
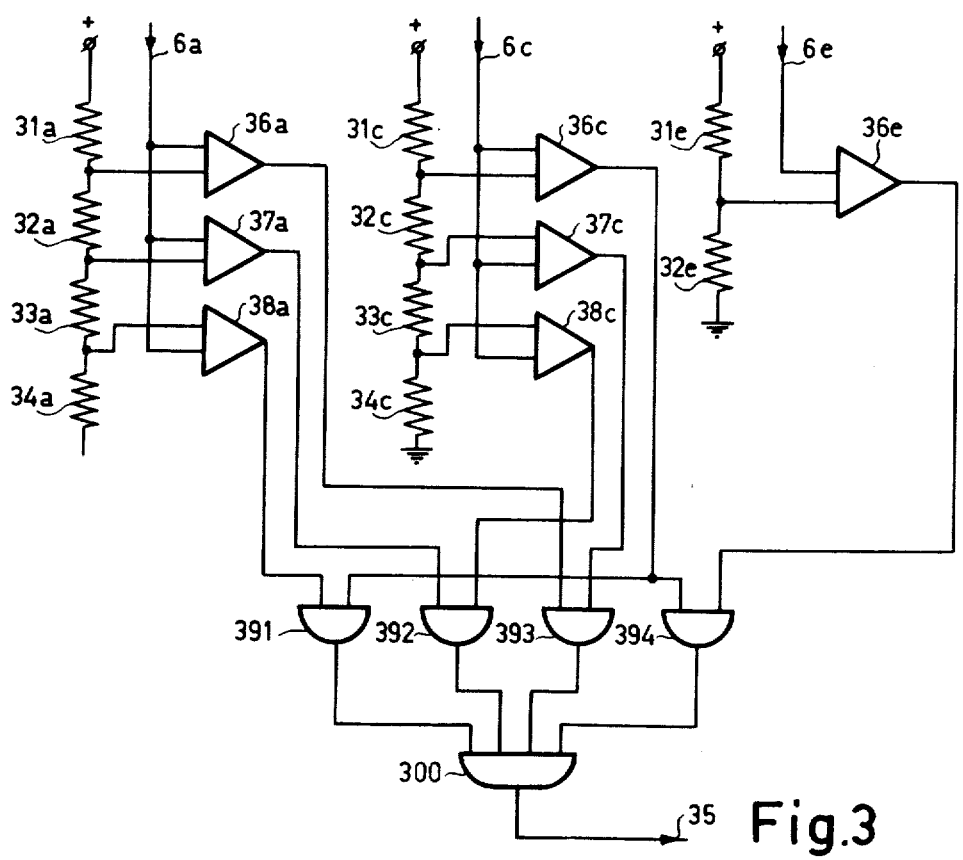
Figure 4:
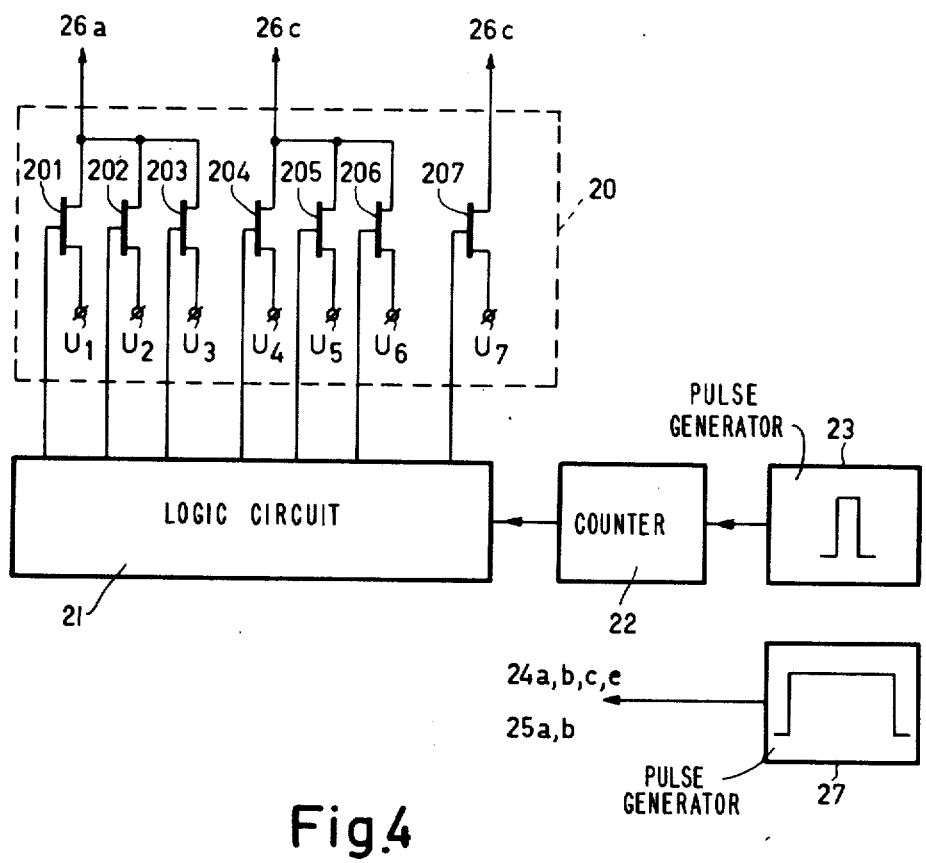

The invention will be described in detail hereinafter with reference to an embodiment which is shown in the drawing, FIG. 1 is a block diagram comprising two safety-supervisory circuits and one test circuit for an X-ray examining apparatus according to the invention, FIG. 2 shows a safety-supervisory circuit for supervising the synchronous operation of different transducers which can be used in FIG. 1, FIG. 3 shows the construction of a safety-supervisory circuit for supervising the motions of an X-ray examining apparatus, and FIG. 4 shows a block diagram of the test circuit according to FIG. 1.

The safety circuit shown in FIG. 1 tests and supervises — in the case of failure of the operation circuit which is independent thereof — the motions of an X-ray examining apparatus, i.e., the apparatus tilt and the table top movement in the longitudinal direction and the transverse direction. Given limit positions have been adjusted for each of these apparatus motions which are effected by way of a motor. However, the tilting of the apparatus and the table top motion cannot be arbitrarily controlled between these limit positions; between these limit positions so-termed "inhibited regions" exist. This can be illustrated as follows. It is assumed that an X-ray examining apparatus can be tilted between +90° and −90° and that its table top can be slid beyond the foot end as well as beyond the head end. When the table top is not slid out, the apparatus can be tilted to the +90°-position as well as to the −90°-position. In the horizontal position of the examining apparatus (0°-position) the table top can be arbitrarily displaced in the longitudinal direction between the limit positions. However, this is not possible when the apparatus is, for example, in the vertical position in which the head of the patient is directed downwards (−90°). In that case the table top can be displaced beyond the foot end, but not beyond the head end. If the examining apparatus is in the upright position (+90°-position), the table top cannot be displaced beyond the foot end. The present safety circuit has for its object to actuate the switching device (in this case the protection device) as soon as such an "inhibited region" is reached before the operation-supervisory circuit has switched off the drive system.

FIG. 1 shows three drive motors 7a, 7c, 7e which serve for the displacement of the table top in the longitudinal direction (7a), the tilting (7c) and the displacement of the table top in the transverse direction (7e) and which at the same time displace the tapping of each time two potentiometers 4a–4b, 4c–4d, 4e–4f, respectively. The potentiometers 4a, 4c, 4e are connected to a positive direct voltage, whilst the potentiometers 4b, 4d and 4f are connected to a direct voltage of the same value but oppposite polarity. The voltages on the tappings of potentiometers 4a–4b, 4c–4d, and 4e–4f, therefore, are equal but opposed. The tappings of the potentiometers 4a, 4c and 4e are connected, via the leads 6a, 6c and 6e, to the inputs of the synchronisation-supervisory device 1 and, each time via a switch 24a, 24c and 24e, to the position-supervisory device 3. The tappings of the potentiometers 4b, 4d and 4f which are connected to a negative direct voltage are, moreover, connected to the inputs of the synchronisation-supervisory device 1 via the leads 6b, 6d and 6f, a switch 24b being incorporated in the lead 6b.

The synchronisation-supervisory device (to be described in detail hereinafter) checks the synchronous operation of the potentiometers 4a–4b, 4c–4d and 4e–4f by comparing the voltages on the potentiometer tappings which are displaced by the same motor. If the result of the comparison is that the sum of the voltages derived from the potentiometers is not equal to zero, the contact 15 incorporated in the relay network comprising the contacts 25a, 15, 25b and 35 is switched over from the position shown in the drawing by the output signal of the synchronisation-supervisory device 1, with the result that the relay network is interrupted and the protection device 5 which is held via a hold contact 51 and which can be switched on by means of a button 52 when the circuit is put into operation, is cut out, the power supply for the X-ray apparatus then being interrupted in known manner. It is thus checked whether or not the potentiometers 4a to 4f are still operational.

The position-supervisory circuit 3 (to be described in detail hereinafter) serves to establish whether or not the table top is in a so-termed "inhibited region," i.e, whether or not, for example, the table top is slid beyond the foot end when the apparatus in the upright position. If the table top is in such an "inhibited region," the contact 35 in the switching circuit formed by the relay network and the protection device 5 is switched from the position shown in the drawing to a position in which the relay network is interrupted and the protection device is cut-out.

The functioning of the supervisory circuits 1 and 3 is tested by a test circuit 2, the construction of which will be described in detail hereinafter. Test circuit 2 switches over the switches 24a, 24b, 24c and 24e at regular instants. The switching over between the two feasible positions is periodically effected at intervals of 40 ms.

When the switches have been switched over to the position which is not shown in the drawing (test position), the inputs of the position-supervisory circuit 3 are no longer connected to the tapping of the potentiometer 4a, 4c, 4e, respectively, but to the leads 26a, 26c and 26e. The leads 26a, 26c and 26e are connected to a fault-simulation generator which is incorporated in the test circuit 2. This fault-simulation generator generates voltage combinations which correspond to a so-termed inhibited region, and the construction of this generator is such that during the period in which the switches are connected in the test circuit all voltage combinations of the various inhibited regions are generated. When the switch 24b is in its test position, it carries a negative direct voltage of a value which lies between the smallest and the largest value of the voltages occurring on the lead 26a in the test position and which is not equal to any of the voltages generated in the test position. This means that the voltages on the leads 6a and 6b can never be equal in the test position. As will be further elaborated in the description of the synchronisation-test circuit, for the testing of the functioning of this supervisory circuit it is sufficient to apply merely a few unequal voltages in the test position.

The synchronisation-supervisory circuit 1 as well as the position-supervisory circuit 3 thus generate signals in the test position which occur only in the case of a defect in the position shown (operation position). Therefore, in the test position the switches 15 and 35 are switched over to the other position which is not shown in the drawing, with the result that the direct voltage protection would be cut out, even though the supervisory circuits 1 and 3 function. So as to prevent the protection device from being cut out when the supervisory circuits 1 and 3 are switched on, the contacts 25a and 25b are switched to the position not shown in the drawing, simultaneously with the contacts 24a, 24b, 24c and 24e, with the result that the relay network is closed once more. If it occurs in the test position of the switches that one of the contacts 15 or 35 is not switched over, even though voltages which represent a defect or a failure are present on the outputs of the associated supervisory circuit, the relay network is interrupted and the protection device 5 is cut out.

The condition of the potentiometers and the position of the table top are thus supervised in the operating position of the switches 24a, 24b, 24c, 24e and 25a, 25b by means of the supervisory circuits 1 and 3, whilst in the test position 2 the operation of the supervisory circuits 1 and 3 is tested. This multiple check permits of the use of less reliable components, such as potentiometers and the like, which normally cannot be used in a safety circuit because of their comparatively high susceptibility to trouble.

Semiconductors can alternatively be used instead of the relay network. Part of this relay network or the equivalent semiconductor circuit can also be incorporated in the supervisory circuits 1 and 3 and be switched over by the test circuit 2 together with the switches 24a, 24b, 24c, 24e.

The circuits 1, 2 and 3 will be described in detail hereinafter with reference to the block diagrams shown in the FIGS. 2 to 4.

FIG. 2 shows the synchronisation-test circuit according to FIG. 1. The leads 6a. . .6f are connected, via the identical resistors 11a...11f, to the inverting input of an operational amplifier 12 which is fed back via an adjustable resistor 14. Connected to the output of the operational amplifier 12 is a discriminator 13 which switches over the contact 15 (see FIG. 1) when the output signal of the operational amplifier is not equal to zero or lies outside a given range around the zero point of the voltage.

The circuit operates as follows: in the normal operating condition the currents flowing through the resistors 11a–11b, 11c–11d and 11e–11f are equal but opposed, because the voltages on the corresponding leads 6a–6b, 6c–6d and 6e–6f, respectively, are equal and opposed and because the resistors 11a–11f are identical. The resultant voltage or current on the inverting input of the operational amplifier 12, consequently, is zero and so is the voltage on the output of the operational amplifier 12. However, if a defect occurs, i.e., if one of the tappings of the potentiometer is jammed or displaced, the currents are no longer equal and opposed, with the result that on the output of the amplifier 12 a voltage appears which deviates from zero, the said voltage actuating the discriminator 13 which switches over the contact 15. If currents of opposite polarity and of different value flow via the resistors 11a and 11b in the test position of the switches 24a and 24b, the output signal of the operational amplifier is not equal to zero either, with the result that the contact 15 is switched over.

FIG. 3 is a block diagram of the position-supervisory circuit 3. The voltages present on the leads 6a, 6c and 6e are applied to an input of the comparators 36a, 37a and 38a, or 36c, 37c and 38c or 36e, respectively. The other inputs of the comparators 36a, 37a and 38a are connected to a fixed voltage divider incorporating the resistors 31a, 32a, 33a and 34a. Similarly, the second inputs of the comparators 36c, 37c and 38c are connected to the tappings of a voltage divider consisting of fixed resistors 31c, 32c, 33c and 34c, the second input of the comparator 36e being connected to a voltage divider which consists of the two fixed resistors 31e and 32e. The said comparators supply a binary output signal, for example, a logic "1", when the potential on the upper input in the drawing is more positive than the potential on the lower input. Because the voltage on the leads 6a, 6c, 6e (in the operating position) of the switches 24a, 24c, 24e is a measure of the position or the tilt of the table top, a change always occurs in the binary signal on the output of the comparator when a given position or tilt is exceeded (depending on which input of the comparator receives the fixed direct voltage and the direct voltage on the leads 6a, 6c, 6e). For example, on the output of the comparator 37a always a logic "1" appears when the table top is slid slightly beyond the foot end, whilst on the output of the comparator 37c a voltage appears if the table top is tilted 30° or more in the position in which the patient's feet are directed downwards.

The outputs of the comparators 36a, 37a, 38a, 36c, 37c, 38c, and 36e are connected to the output of four add circuits 391, 392, 393 and 394. The fixed voltages have a value such and the connections have been chosen such that each time when the table top arrives in a so-termed inhibited region, a "1"-pulse appears twice on the input of one of the add circuits 391...394, with the result that a "1" also appears on the output of this add circuit; each add circuit then signals one of the relevant inhibited regions. Such an inhibited region is, for example, the region in which the table top is situated when it is slightly slid beyond the foot end whilst the table is tilted more than 30° in the position in which the feet of the patient are directed downwards. The signal "1" is then present on the output of the comparators 37a and 37c, the said comparators also generating the signal "1" on the output of the add circuit 393. The outputs of the add circuits 391...394 are connected to the inputs of a selection circuit 300 which always supplies an output signal which switches over the contact 35 when one of the add circuits signals an "inhibited region."

FIG. 4 shows details of a test circuit 2 according to FIG. 1. A pulse generator 23 which supplies pulses having a duration of, for example, 10 ms controls a counter 22 which counts from 1 to 8. The counter outputs control a logic circuit 21 which renders one or more of the field-effect transistors 201...207 incorporated in the switching device 20 conductive. The logic circuit is constructed such that at the most one of transistors 201...207 is conductive. If one of the field-effect transistors is conductive, the lead 26a, 26b or 26c connected thereto has the potential ($U_1...U_7$) which is present on a source electrode. Via the switches 24a, 24b, 24c and 24e and the leads 6a...6e (see FIG. 1), these potentials switch over at least one of the comparators connected thereto. For example, if during a 10-ms pulse the logic circuit 21 supplies output voltages which render the field-effect transistors 203 and 205 conductive, for example, the comparators 36a, 37a and 37c are switched over, i.e, a "1" appears on their output, with the result that on the output of the add circuit 393 which is connected to the comparators 36a and 37c a "1" also appears which causes the switching over of the contact 35 via the selection circuit 300. During the next 10-ms pulse other field-effect transistor switches become conductive, with the result that a different voltage combination appears on the lines 26a, 26c and 26e which, however, also corresponds to an inhibited region. Successive voltage combinations are thus generated which successively activate the add circuits 391...394. If one of these add circuits or one of these comparators is defective, the switching contact 35 is not switched over in the test position of the switches 25a and 25b, with the result that the relay network is interrupted and the protection device is cut out.

Because the voltages $U_1$, $U_2$ and $U_3$ can have a value which is larger or smaller than that of the direct voltage present on the lead 6b in the test position of the switch 24b, the sum of the voltages or the currents flowing through the leads 6a and 6b is not equal to zero. During the fault simulation, i.e., in the test position of the switches 24a, 24b, 24c, 24e and 25a, 25b, an output signal should appear on the output of the synchronisation-test circuit 1 which holds the contact 15 in the position which is not shown in FIG. 1. If this synchronisation-test circuit is defective, the contact 15 remains in the position shown in FIG. 1, with the result that the relay network is also interrupted and the protection device is cut out. The test circuit 2, moreover, comprises a pulse generator 27 which supplies pulses of a duration of 40 ms which switch over the switches 24a, 24b, 24c, 24e and 25a, 25b in the rhythm of 40-ms. These 40-ms pulses could in principle also be derived from the pulse generator 23, but the use of two independent pulse generators offers the advantage that the safety circuit is also activated if one of the two generators breaks down.

What is claimed is:

1. In X-ray examining apparatus having a supervisory circuit that monitors the output voltage from a transducer, said supervisory circuit having an output that actuates a switch indicating a fault when said output voltage from said transducer lies within a predetermined range that corresponds to a failure, the improvement comprising a test circuit for periodically testing whether said supervisory circuit is properly functioning and for actuating said switch indicating a fault when said supervisory circuit is not properly functioning, said test circuit comprising means for generating a voltage which lies within said predetermined range to simulate the corresponding failure, switching means for periodically applying said generated voltage to said supervisory circuit in place of the output voltage from said transducer and means synchronized with said switching means for logically complementing said output of said supervisory circuit during the periodic application of said generated voltage to said supervisory circuit, whereby said switch indicating a fault is actuated during the periodic application of said generated voltage only if said output of said supervisory circuit then does not indicate a failure and during any other time only if said output does indicate a failure.

* * * * *